(12) United States Patent
Edelman

(10) Patent No.: US 8,574,612 B2
(45) Date of Patent: Nov. 5, 2013

(54) MEDICAL DEVICES HAVING A COATING OF BIOLOGIC MACROMOLECULES

(75) Inventor: Peter Edelman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 766 days.

(21) Appl. No.: 12/708,993

(22) Filed: Feb. 19, 2010

(65) Prior Publication Data

US 2010/0226953 A1 Sep. 9, 2010

Related U.S. Application Data

(60) Provisional application No. 61/157,377, filed on Mar. 4, 2009.

(51) Int. Cl.
*A61F 2/12* (2006.01)
*A61K 38/02* (2006.01)

(52) U.S. Cl.
USPC .......................... 424/422; 424/423; 424/93.6

(58) Field of Classification Search
None
See application file for complete search history.

(56) References Cited

U.S. PATENT DOCUMENTS

| | | | |
|---|---|---|---|
| 5,487,897 A * | 1/1996 | Polson et al. ............... | 424/426 |
| 5,733,925 A | 3/1998 | Kunz et al. | |
| 5,744,515 A | 4/1998 | Clapper | |
| 5,824,049 A | 10/1998 | Ragheb et al. | |
| 6,156,572 A | 12/2000 | Bellamkonda et al. | |
| 6,428,579 B1 | 8/2002 | Valentini | |
| 7,037,332 B2 | 5/2006 | Kutryk et al. | |
| 7,311,980 B1 | 12/2007 | Hossainy et al. | |
| 7,314,480 B2 | 1/2008 | Eidenschink et al. | |
| 7,367,989 B2 | 5/2008 | Eidenschink | |
| 7,637,941 B1 | 12/2009 | Manicka et al. | |
| 2003/0087111 A1 | 5/2003 | Hubbell et al. | |
| 2005/0043787 A1 | 2/2005 | Kutryk et al. | |
| 2005/0147647 A1 | 7/2005 | Glauser et al. | |
| 2005/0149161 A1 | 7/2005 | Eidenschink et al. | |
| 2005/0154442 A1 | 7/2005 | Eidenschink et al. | |
| 2005/0158405 A1 | 7/2005 | Boukas | |
| 2005/0187146 A1 | 8/2005 | Helmus et al. | |
| 2005/0240145 A1 | 10/2005 | Scott et al. | |
| 2005/0266040 A1 | 12/2005 | Gerberding | |
| 2006/0051395 A1 | 3/2006 | Beyer et al. | |
| 2006/0052862 A1 | 3/2006 | Kanamaru et al. | |
| 2006/0067909 A1 | 3/2006 | West et al. | |
| 2008/0057097 A1 | 3/2008 | Benco et al. | |
| 2009/0149942 A1 | 6/2009 | Edelman et al. | |

FOREIGN PATENT DOCUMENTS

| | | |
|---|---|---|
| EP | 0512122 A1 | 11/1992 |
| EP | 1632258 A2 | 3/2006 |
| JP | 2006-068378 A | 3/2006 |
| WO | 92/09312 A1 | 6/1992 |

OTHER PUBLICATIONS

Japanese Patent Office; Office Action in Japanese patent application No. 2009-527366, dated Mar. 6, 2012.
Communication Relating to the Results of the Partial international Search, from PCT/US2007/019109, Mailed: May 19, 2009.
International Search Report and Written Opinion, from PCT/US2007/019109, mailed: Jun. 17, 2009.
Lin, Horng-Ban, et al, "Synthesis, surface, and cell-adhesion properties of polyurethanes containing covalently grafted RGD-peptides," Journal of Biomedical Materials Research, vol. 28, No. 3 pp. 329-342 (1994).
Lestini, Brian J., et al., "Surface modification of liposomes for selective cell targeting in cardiovascular drug delivery," Journal of Controlled Release, vol. 78, Nos. 1-3, pp. 235-247 (2002).
Baker, John E., et al., "Fibrin Coated Stents as a Depot to Deliver RGD Peptide Inhibit Vascular Reaction in Atherosclerotic Rabbit Model," Journal of the American College of Cardiology, vol. 27, No. 2, p. 197 (1996).
Vadgama, Ed., Surfaces and Interfaces for Biomaterials, Woodhead Publishing LTD., Cambridge, England (2005) p. 770 and cover page (2 pages).
Sever et al., "Absorption Spectroscopy and Binding Constants for First-Row Transition Metal Complexes of a DOPA-Containing Peptide," © 2006 Royal Society of Chemistry, Dalton Transactions, 2006, pp. 813-822.
Tsai et al., "Gold nanoparticle-based competitive colorimetric assay for detection of protein-protein interactions," Chem. Commun., 2005, p. 4273-4275.
Razatos et al., "Molecular Determinants of Bacterial Adhesion Monitored by Atomic Force Microscopy," Proc. Natl. Acad. Sci., © 1998 Natl. Acad. Sci. USA; vol. 95, pp. 11059-11064, Sep. 1998, Applied Biological Sciences.
Statz et al., "New Peptidomimetic Polymers for Antifouling Surfaces," © 2005 J. Am. Chem. Soc. 127, pp. 7972-7973.
Zucher et al., "Biornimemtic Surface Modifications based on the Cyanobacterial Iron Chelator Anachelin," © 2006 J. Am. Chem. Soc., 128, pp. 1064-1065.
Hu et al., "Protection of 3,4-dihydroxyphenylalanine (DOPA) for Fmoc Solid-Phase Peptide Synthesis," © 2000 Elsevier Science Ltd., Tetrahedron Letters 41, 2000, pp. 5795-5798.
Fishbein et al., "Bisphosphonate-Mediated Gene Vector Delivery from the Metal Surfaces of Stents," Proc. Natl. Acad. Sci., © 2005 Natl. Acad. Sci. USA; vol. 103, pp. 159-164, Jan. 3, 2003.
Willet et al., "Differential adhesion of amino acids to inorganic surfaces," Proc. Natl. Acad. Sci. 102(22), 2005, pp. 7817-7822.

(Continued)

*Primary Examiner* — Yunsoo Kim
(74) *Attorney, Agent, or Firm* — Kenyon & Kenyon LLP

(57) ABSTRACT

A medical device having a coating of biologic macromolecules. The coating of biologic macromolecules is protected by a temporary protective layer disposed over the biologic macromolecules. The temporary protective layer serves to protect the structure (e.g., conformation) and/or function (e.g., target binding capacity) of the biologic macromolecules during processing, storage, handling, and/or delivery (e.g., implantation or insertion into a patient) of the medical device. Upon implantation or insertion into a patient's body, the temporary protective layer may dissolve to expose the biologic macromolecules to the physiologic environment.

14 Claims, 1 Drawing Sheet

(56) References Cited

OTHER PUBLICATIONS

Tosatti et al., "Peptide Functionalized poly(L-lysine)-g-poly(ethylene glycol) on Titanium, Resistance to protein Adsorption in full Heparinized Human Blood Plasma," © 2003 Elsevier Ltd., Biomaterials 24 (2003) pp. 4949-4958.

Ellis-Behnke et al., "Nano Neuro Knitting: Peptide Nanofiber Scaffold for Brain Repair and Axon Regeneration with Functional Return of Vision," Proc. Natl. Acad. Sci., © 2006 Natl. Acad. Sci. USA vol. 103, pp. 5054-5059, Mar. 28, 2006.

V. Gauvreau et al., "Micropattern printing of adhesion, spreading, and migration peptides on poly(tetrafluoroethylene) films to promote endothelialization," Bioconjugate Chem., Sep.-Oct. 2005 16(5), pp. 1088-1097.

Boateng et al., "RGD and Y7GSR Synthetic Peptides Facilitate Cellular Adhesion Identical to That of Laminin and Fibronectin but Alter the Physiology of Neonatal Cardiac Myocytes," Am. J. Physiol.-Cell Physiol. 288, 2005, pp. 30-38.

L. Holle et al., "In vitro targeted killing of human endothelial cells by co-incubation of human serum and NGR peptide conjugated human albumin protein bearing alpha (1-3) galactose epitopes," Oncol. Rep. Mar. 2004; 1 1(3): pp. 613-616.

R.G. Flemming et al., "Effects of synthetic micro- and nano-structured surfaces on cell behavior," Biomaterials 20, 1999, pp. 955-962.

N. Fujisawa et al., "A novel textured surface for blood-contact," Biomaterials 20, 1999, pp. 955-962.

Michel et al., "Selective Molecular Assembly Patterning: A New Approach to Micro- and Nanochemical patterning of Surfaces for biological applicants," © xxxx American Chemical Society, page est: 6.2 (7 pages).

Van Alsten, Self-Assembled Monolayers on Engineering Metals: Structure, Derivation, and Utility, Langmuir 15: 1999, pp. 7605-7614.

Doraiswamy et al., "Laser Thin Film Processing of Biopolymers: Mussel Adhesive Protein Analog," Mater. Res. Soc. Symp. Proc., © 2006 Materials Research Society, vol. 897E, pp. 2.1-2.6.

Lee et al., "Single-molecule mechanics of mussel adhesion," Proc. Natl. Acad. Sci., © 2006 Natl. Acad. Sci. USA; vol. 103, pp. 12999-13003, Aug. 29, 2006.

"Study Reveals Details of Mussels' Tenacious Bonds," Science Daily, © 1995-2008 ScienceDaily LLC, Aug. 16, 2006, available at: http://www.sciencedaily.com/releases/2006/08/060816024159.htm.

Kouvroukoglou et al., "Endothelial Cell Migration on Surfaces Modified with Covalently-Bound Adhesive Peptides," Biomaterials, 21 (2000): 1725-1733.

Van Belle et al. ("Stent Endothelialization: Time Course, Impact of Local Catheter Delivery, Feasibility of Recombinant Protein Administration, and Response to Cytokine Expedition." Circulation, 197, 95, pp. 438-448), 2006.

Zilberman ("Dexamethasone loaded bioresorbable films used in medical support devices: Structure, degradation, crystallinity and drug release," Acta Biomaterialia, 2005, 1, 615-624.

Hansson, et al., "Whole blood coagulation on protein adsorption-resistant PEG and peptide functionalised PEG-coated titanium surfaces", Biomaterials, vol. 26, pp. 861-872, (2005).

Jun, et al., "Development of a YIGSR-peptie-modified polyurethaneurea to enhance endothelialization", J. of Biomaterials Science, vol. 15, No. 1, pp. 73-94, (2004).

Willats, "Phage display: practicalities and prospects", Plant Molecular Biology, vol. 50, No. 6, pp. 837-854, (Dec. 2002).

* cited by examiner

MEDICAL DEVICES HAVING A COATING OF BIOLOGIC MACROMOLECULES

CROSS REFERENCE TO RELATED APPLICATION

The present application claims priority to U.S. provisional application Ser. No. 61/157,377 filed Mar. 4, 2009, the disclosure of which is incorporated herein by reference in its entirety.

TECHNICAL FIELD

The present invention relates to medical devices having bioactive coatings thereon.

BACKGROUND

A problem that has at times arisen with the use of vascular stents is reocclusion (restenosis) of the blood vessel after stent implantation. An important factor contributing to restenosis is the injury to or loss of the natural protective lining of endothelial cells on the inner surface of the artery as a result of stent implantation. This loss of the endothelial cell lining denudes the arterial wall, making it vulnerable to thrombosis, infection, scarring, or abnormal tissue growth. Thus, reestablishing a layer of endothelial cells (re-endothelialization) in the stented artery is thought to be important in improving the long-term biocompatibility of the stent. To promote effective endothelialization, however, endothelial cells must migrate from adjacent areas of the artery and adhere onto the surface of the stent.

One proposed approach to promoting re-endothelialization is by providing a surface coated with biologic macromolecules, such as antibodies, to serve as an attachment substrate for endothelial cells. However, in their naturally occurring hydrated state, antibodies and other proteins commonly exist in a complex, folded conformation (i.e., their tertiary structure). This complex, folded conformation of the biologic macromolecules can be disrupted during processing, storage, handling, and/or delivery of the stent, which can result in deactivation of the biologic macromolecules (e.g., due to denaturation from heat or moisture exposure during sterilization of the stent). Thus, there is a need for an improved coating of biologic macromolecules for medical devices.

SUMMARY

In another aspect, the present invention provides a medical device having a coating, the coating comprising: biologic macromolecules disposed over a surface of the medical device; and a temporary protective layer disposed over at least a portion of the biologic macromolecules, the temporary protective layer comprising a water-soluble material, and wherein the temporary protective layer substantially dissolves within 24 hours after implantation or insertion of the medical device in a patient.

In another aspect, the present invention provides a method for making a medical device, comprising: providing a medical device; disposing biologic macromolecules over a surface of the medical device; and disposing a low molecular weight carbohydrate over the biologic macromolecules.

BRIEF DESCRIPTION OF THE DRAWINGS

FIG. 1A shows the stent surface with a coating of antibodies. FIG. 1B shows the stent surface with the antibodies protected by a temporary protective layer. FIG. 1C shows the stent surface after dissolution of the temporary protective layer.

DETAILED DESCRIPTION

Figure 1A:
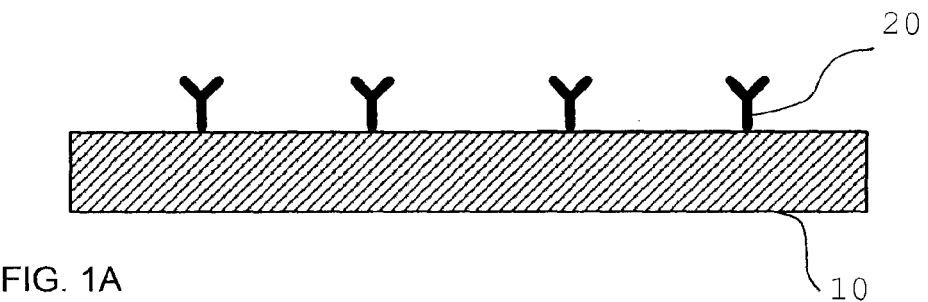
FIGS. 1A-1C show a coating of antibodies on a portion of a stent according to an embodiment of the present invention.

In one aspect, the present invention provides a medical device having a coating of biologic macromolecules. The biologic macromolecules are protected by a temporary protective layer disposed over the biologic macromolecules (e.g., the biologic macromolecules may be disposed under or contained in the temporary protective layer). The temporary protective layer serves to protect the structure (e.g., conformation) and/or function (e.g., target binding capacity) of the biologic macromolecules during processing, storage, handling, and/or delivery (e.g., implantation or insertion into a patient) of the medical device. Upon implantation or insertion into a patient's body, the temporary protective layer is designed to dissolve to expose the biologic macromolecules to the physiologic environment.

As used herein, the term "biologic macromolecule" refers to a medium to large molecular weight organic molecule that is present in a biological sample or is a synthetic derivative thereof. As such, biologic macromolecules include antibodies, peptides, polypeptides, proteins, glycoproteins, enzymes, oligosaccharides, lipids, and nucleic acids (e.g., DNA or RNA).

In some cases, the biologic macromolecules provide a substrate for the adhesion of endothelial cells onto the medical device. As used herein, the term "endothelial cells" includes endothelial progenitor cells. Various types of biologic macromolecules are capable of providing a substrate for the adhesion of endothelial cells (e.g., cell adhesion polypeptides or antibodies).

In certain embodiments, the biologic macromolecules may be antibodies that are capable of binding endothelial cells (e.g., by being directed to a cell surface component of endothelial cells). As used herein, the term "antibody" refers to an immunoglobulin, whether produced naturally or synthetically (e.g. recombinant), either in whole or in part. The term antibody also encompasses antibody fragments, which refers to any derivative of an antibody that is less than full length while retaining at least a portion of the full-length antibody's specific binding ability. Examples of antibody fragments include, but are not limited to, Fab, Fab', F(ab)2, F(ab') 2, Fv, dsFv, single-chain Fvs (scFv), diabodies, and bispecific antibodies. The fragment can include multiple chains linked together. As used herein, an Fv antibody fragment is composed of one variable heavy domain (VH) and one variable light (VL) domain linked by noncovalent interactions. As used herein, a dsFv refers to an Fv with an engineered intermolecular disulfide bond which stabilizes the VH-VL pair. As used herein, scFv refer to antibody fragments that contain a variable light chain (VL) and variable heavy chain (VH) covalently bonded by a polypeptide linker in any order. The linker is of a length such that the two variable domains are bridged without substantial interference. Exemplary linkers are (Gly-Ser)$_n$ residues with some Glu or Lys residues dispersed throughout to increase solubility. As used herein, diabodies are dimeric scFv.

Hence, as used herein, an "antibody" includes any protein having a binding domain that is homologous or substantially homologous to an immunoglobulin binding domain. The antibodies can be monoclonal antibodies (including full length monoclonal antibodies), polyclonal antibodies, or multispecific antibodies (e.g., bispecific antibodies). Antibodies include members of any immunoglobulin class, including IgG, IgM, IgA, IgD, and IgE.

In certain embodiments, the biologic macromolecules are cell adhesion polypeptides that are capable of binding endothelial cells. The cell adhesion polypeptides may be any of the proteins of the extracellular matrix which are known to play a role in cell adhesion, including fibronectin, vitronectin, laminin, elastin, fibrinogen, collagen types I, II, and V, as described in Boateng et al., *RGD and YIGSR Synthetic Peptides Facilitate Cellular Adhesion Identical to That of Laminin and Fibronectin But Alter the Physiology of Neonatal Cardiac Myocytes*, Am. J. Physiol.—Cell Physiol. 288:30-38 (2005), which is incorporated by reference herein. Additionally, the polypeptides may be any peptide derived from any of the aforementioned proteins, including fragments or sequences containing the binding domains. Such peptides include those having integrin-binding motifs, such as the RGD (arginine-glycine-aspartate) motif, the YIGSR (tyrosine-isoleucine-glycine-serine-arginine) motif, and related peptides that are functional equivalents. The peptides may also be any of the peptides described in U.S. Patent Publication No. 2006/0067909 (West et al.), which is incorporated by reference herein.

The biologic macromolecules may be disposed on a surface of the medical device by using any suitable coating method known in the art, including conventional coating techniques such as spray coating, electrostatic spray coating, and dip coating. The biologic macromolecules may be disposed on or within various types of surfaces on the medical device. In certain embodiments, the surface is the bare, uncoated surface of the medical device. The bare surface of the medical device may be smooth or porous, such as the porous stent surface described in U.S. Patent Publication No. 2005/0266040 (Gerberding), which is incorporated by reference herein. Where the surface is porous, the biologic macromolecules may be deposited within the pores of the porous surface. In other embodiments, the surface of the medical device may be the surface of another coating on the medical device, such as a polymer coating.

Other coating methods may also be used, including methods involving surface adsorption of the biologic macromolecules onto the substrate. The biologic macromolecules may be adsorbed onto the substrate through non-covalent interactions, such as hydrogen bonding, metal coordination, hydrophobic forces, van der Waals forces, pi-pi interactions, or electrostatic effects. For example, the biologic macromolecules may form a monolayer through a molecular self-assembly processes. In such cases, there may be a single attachment point to the substrate per biologic macromolecule such that a monolayer of the biologic macromolecules self-assembles on the substrate.

The temporary protective layer serves to protect the biologic macromolecules during processing, storage, handling, and/or delivery (e.g., implantation or insertion into a patient) of the medical device. For example, the temporary protective layer may serve to protect the biologic macromolecules during prolonged periods of elevated temperature or humidity, during periods of desiccation, during a freeze-drying process, during sterilization of the medical device (e.g., by heat or chemicals), or during delivery to the target site (e.g., during scraping against rough, calcified lesions in a blood vessel or against parts of a catheter delivery system). During delivery to the target site, the temporary protective layer may also serve to provide lubricity to the medical device as the temporary protective layer becomes hydrated. Upon implantation or insertion of the medical device into a patient's body, the biologic macromolecules may be reconstituted by exposure to an aqueous environment (e.g., physiologic fluid).

Upon implantation or insertion into a patient's body, the temporary protective layer dissolves to expose the biologic macromolecules to the physiologic environment. To allow for rapid activation of the biologic macromolecules, in some cases, the temporary protective layer is designed to substantially dissolve within 24 hours; and in some cases, within 6 hours; and in some cases, within 1 hour after implantation or insertion of the medical device in the patient's body. Other dissolution rates are possible, depending upon the particular application. The dissolution rate of the temporary protective layer may be controlled by adjusting various factors such as the composition, structure, and/or thickness of the temporary protective layer.

The temporary protective layer may comprise any suitable water-soluble material. As used herein, the term "water-soluble" means substantially soluble in water. Such materials include proteins, peptides, amino acids, carbohydrates, lyotropic salts, or combinations thereof. Examples of proteins that can be used in the temporary protective layer include serum albumin such as human serum albumin (HSA), recombinant human albumin (rHA), gelatin, casein, and the like. Examples of lyotropic salts include sulfates, phosphates, citrates, magnesium (e.g., magnesium sulfate), sodium, calcium, potassium, ammonium, or mixtures thereof.

In certain embodiments, the temporary protective layer comprises a carbohydrate. This feature may be useful because the hydroxy groups on the carbohydrates substitute for the water molecules that are hydrogen-bonded to the biologic macromolecules, which would otherwise denature during drying due to the loss of structural support provided by the hydrogen-bonded water molecules. Denaturing may also be caused by the exchange of inter-molecular hydrogen bonding with intra-molecular hydrogen bonding. Denaturing of the biologic macromolecules may lead to an irreversible loss of tertiary or quaternary structure, which can cause loss of function. As used herein, the term "carbohydrates" includes, but is not limited to, monosaccharides, disaccharides, trisaccharides, oligosaccharides, polysaccharides, and derivatives of sugars (such as sugar alcohols, sugar acids, esterified sugars, and sugar polymers (e.g., Ficoll™)). The carbohydrates may be in the D and/or L forms.

In some cases, the carbohydrate is a non-reducing carbohydrate. This feature may be useful in avoiding undesirable reactions of the carbohydrate with the biologic macromolecules (e.g., glycation of the biologic macromolecules). Such non-reducing carbohydrates include sucrose, fructose, mannose, trehalose, and raffinose.

The molecular weight of the carbohydrate will vary depending upon the particular application. In some cases, the carbohydrate is a low molecular weight carbohydrate (i.e., having a molecular weight of 1,000 or less), such as a monosaccharide or a disaccharide. The temporary protective layer may also include other pharmaceutically-acceptable excipients, which may serve as diluents, binders, stabilizers, buffers, surfactants, adjuvants, or the like.

In certain embodiments, the temporary protective layer comprises a low to medium molecular weight polymer or copolymer of ethylene oxide and/or propylene oxide, including polyethylene glycol. This class also includes triblock copolymers of polypropylene oxide) and poly(ethylene oxide), also known as poloxamers and sold as Pluronics® (BASF).

The thickness of the temporary protective layer will vary depending upon the particular application and taking into consideration such factors as the desired level of flexibility or hardness. In some cases, the thickness of the temporary protective layer is in the range of 0.25-20 µm, and in some cases, in the range of 0.5-10 µm. In some cases, the temporary protective layer may be sufficiently thick to protect the coating of biologic macromolecules from mechanical abrasion that may occur during delivery to the target site (e.g., scraping against rough, calcified lesions in a blood vessel or against parts of a catheter delivery system). For example, the thickness of the temporary protective layer may be in the range of 5 to 15 µm.

The amount of water-soluble material used in the temporary protective layer relative to the amount of the biologic macromolecules will vary depending upon the particular application. In some cases, the mass ratio of the water-soluble material relative to the biologic macromolecules is in the range of 1:10 to 100:1.

The temporary barrier layer may be applied onto the medical device using any known method of applying coatings to the surfaces of medical devices, including spray coating or dip coating. In some cases, the coating of biologic macromolecules and the temporary barrier layer may be formed together. For example, the biological macromolecules and the material used in the temporary protective layer may be admixed in a solution, with the solution being deposited onto the medical device. In some embodiments, the biologic macromolecules are formed as a monolayer on the surface of the medical device.

The medical devices of the present invention may further include a therapeutic agent. The therapeutic agent may be carried on or within any component of the medical device, including on or within the temporary protective layer, the coating of biologic macromolecules, or other polymer coating on the medical device.

Figure 1B:
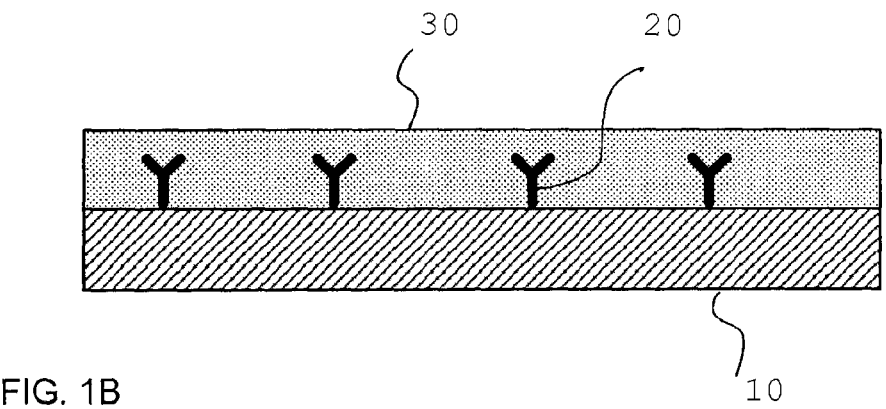
Figure 1C:
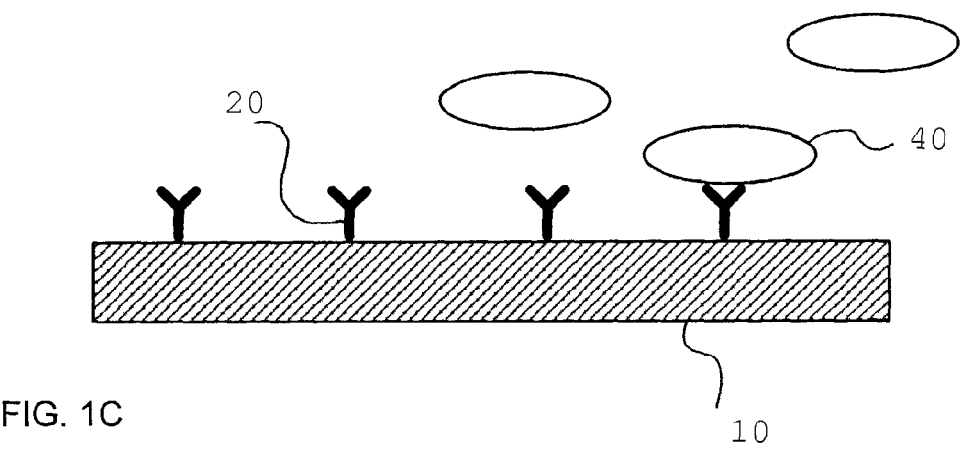

Referring to the embodiment shown in FIGS. 1A-1C, the surface of a portion of stent 10 is coated with antibodies 20 that are capable of binding endothelial cells (e.g., via a cell surface molecule exhibited by endothelial cells). Antibodies 20 may be affixed onto the surface of stent 10 using various methods known in the art, including the method used to make the antibody-coated stents described in U.S. Patent Publication No. 2005/0043787 (Kutryk et al.), which is incorporated by reference herein. For example, stent 10 may be coated with an antibody binding matrix formed of synthetic materials (e.g., polyurethane, segmented polyurethane-urea/heparin, polylactic acid, cellulose ester, or polyethylene glycol) or naturally occurring materials (e.g., collagen, laminin, heparin, fibrin, cellulose, or carbon). Antibodies 20 are tethered onto the matrix by either covalent or non-covalent bonding.

To protect antibodies 20, a temporary protective layer 30 is disposed over antibodies 20. Temporary protective layer 30 is formed by depositing a solution containing trehalose (a non-reducing sugar which is particularly suitable for providing conformation stabilizing hydrogen-bonding with the biologic macromolecule) onto antibodies 20, and allowing the solution to dry. The solution may also contain other excipient materials, such as buffering agents, surfactants, binders, or other additives.

In operation, stent 10 is implanted into a patient's body. Upon implantation, temporary protective layer 30 undergoes dissolution (e.g., within a period of 24 hours) such that antibodies 20 are exposed. This allows endothelial cells 40 that migrate onto stent 10 to adhere to antibodies 20.

Non-limiting examples of medical devices that can be used with the present invention include stents, stent grafts, catheters, guide wires, neurovascular aneurysm coils, balloons, balloon catheters, filters (e.g., vena cava filters), vascular grafts, intraluminal paving systems, pacemakers, electrodes, leads, defibrillators, joint and bone implants, spinal implants, access ports, intra-aortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

A therapeutic agent used in the present invention may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, and smooth muscle cells. Other therapeutic agents that may be used with the present invention are disclosed in U.S. Patent Publication No. 2008/0107794 (O'Connor et al.), which is incorporated by reference herein.

The foregoing description and examples have been set forth merely to illustrate the invention and are not intended to be limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention.

What is claimed is:

1. A medical device having a coating, the coating comprising:
    biologic macromolecules disposed over a surface of the medical device, wherein the biologic macromolecules are capable of binding endothelial cells; and
    a temporary protective layer disposed over at least a portion of the biologic macromolecules, the temporary protective layer comprising a water-soluble low molecular weight carbohydrate, and wherein the temporary protective layer substantially dissolves within 24 hours after implantation or insertion of the medical device in a patient.

2. The medical device of claim 1, wherein the biologic macromolecules are antibodies that are directed to a cell surface component of endothelial cells.

3. The medical device of claim 1, wherein the biologic macromolecules form a monolayer.

4. The medical device of claim 1, wherein the low molecular weight carbohydrate is a monosaccharide or a disaccharide.

5. The medical device of claim 1, wherein the carbohydrate is a non-reducing carbohydrate.

6. The medical device of claim 1, wherein the temporary protective layer substantially dissolves within 6 hours after implantation or insertion of the medical device in a patient.

7. The medical device of claim 1, wherein the thickness of the temporary protective layer is in the range of 0.5 to 10 µm.

8. The medical device of claim 1, wherein the medical device is a stent.

9. The medical device of claim 1, wherein the medical device is a balloon catheter, and wherein the surface is the surface of a balloon on the balloon catheter.

10. A medical device having a coating, the coating comprising:
   a monolayer of antibodies disposed over a surface of the medical device, wherein the antibodies are directed to a cell surface component of endothelial cells; and
   a temporary protective layer disposed over at least a portion of the monolayer of antibodies, the temporary protective layer comprising a monosaccharide or a disaccharide, and wherein the temporary protective layer substantially dissolves within 6 hours after implantation or insertion of the medical device in a patient.

11. The medical device of claim 1, wherein the low molecular weight carbohydrate is a monosaccharide or a disaccharide, and the temporary protective layer substantially dissolves within 6 hours after implantation or insertion of the medical device in a patient.

12. The medical device of claim 11, wherein the low molecular weight carbohydrate is a non-reducing monosaccharide or a non-reducing disaccharide.

13. The medical device of claim 11, wherein the temporary protective layer substantially dissolves within one hour after implantation or insertion of the medical device in a patient.

14. The medical device of claim 12, wherein the temporary protective layer substantially dissolves within one hour after implantation or insertion of the medical device in a patient.

* * * * *